(12) United States Patent
Kerr

(10) Patent No.: US 9,554,844 B2
(45) Date of Patent: *Jan. 31, 2017

(54) OPEN VESSEL SEALING INSTRUMENT AND METHOD OF MANUFACTURING THE SAME

(71) Applicant: COVIDIEN LP, Mansfield, MA (US)

(72) Inventor: Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/017,774

(22) Filed: Feb. 8, 2016

(65) Prior Publication Data

US 2016/0151110 A1 Jun. 2, 2016

Related U.S. Application Data

(63) Continuation of application No. 13/306,553, filed on Nov. 29, 2011, now Pat. No. 9,265,565.

(51) Int. Cl.
*A61B 17/285* (2006.01)
*A61B 18/14* (2006.01)
(Continued)

(52) U.S. Cl.
CPC .. *A61B 18/1442* (2013.01); *A61B 2017/00526* (2013.01); *A61B 2018/0063* (2013.01);
(Continued)

(58) Field of Classification Search
CPC ............ A61B 18/1442; A61B 18/1445; A61B 18/1452; A61B 18/1455; A61B 2018/1452; A61B 2018/1455; A61B 2090/031; A61B 2090/034; A61B 2017/00526; A61B 2018/0063; Y10T 29/49947
(Continued)

(56) References Cited

U.S. PATENT DOCUMENTS 1,604,695 A 10/1926 Hein
D249,549 S 9/1978 Pike
(Continued)

FOREIGN PATENT DOCUMENTS

CN 201299462 9/2009
DE 2415263 A1 10/1975
(Continued)

OTHER PUBLICATIONS

U.S. Appl. No. 13/185,593, filed Jul. 19, 2011, James D. Allen, IV.
(Continued)

*Primary Examiner* — Christopher D Koharski
*Assistant Examiner* — Michael Carey

(57) ABSTRACT

An open electrosurgical forceps is provided and includes a pair of first and second shaft members each having a jaw member at a distal end thereof. The jaw members are movable from a first position in spaced relation relative to one another to a subsequent position wherein the jaw members cooperate to grasp tissue therebetween. A cutting mechanism is adapted to selectively and removably couple to one of the first and second shaft members. The cutting mechanism includes a cutting trigger for selectively advancing a knife blade extending therefrom through a knife channel defined along one or both of the jaw members. The first shaft member includes a stop feature formed thereon and the second shaft feature includes a stop member formed thereon. The stop feature and stop member configured to selectively engage one another to limit rotation of the first and second shaft members with respect to one another.

12 Claims, 3 Drawing Sheets

(51) Int. Cl.
*A61B 17/00* (2006.01)
*A61B 18/00* (2006.01)

(52) U.S. Cl.
CPC . *A61B 2018/1455* (2013.01); *A61B 2090/031* (2016.02); *A61B 2090/034* (2016.02); *Y10T 29/49947* (2015.01)

(58) Field of Classification Search
USPC .............................................. 606/45, 50, 51
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 4,971,067 A | 11/1990 | Bolduc et al. | |
| 4,985,034 A | 1/1991 | Lipton | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| 6,053,927 A | 4/2000 | Hamas | |
| D424,694 S | 5/2000 | Tetzlaff et al. | |
| D425,201 S | 5/2000 | Tetzlaff et al. | |
| 6,110,171 A * | 8/2000 | Rydell | A61B 18/1442 606/48 |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 9,265,565 B2 * | 2/2016 | Kerr | A61B 18/1442 |
| 2003/0181910 A1 | 9/2003 | Dycus et al. | |
| 2004/0181169 A1 | 9/2004 | Diamond et al. | |
| 2005/0107785 A1 | 5/2005 | Dycus et al. | |
| 2005/0119655 A1* | 6/2005 | Moses | A61B 18/1442 606/51 |
| 2009/0254081 A1* | 10/2009 | Allison | A61B 18/1442 606/39 |
| 2010/0063500 A1 | 3/2010 | Muszala | |
| 2014/0155878 A1* | 6/2014 | Trees | A61B 17/295 606/33 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 200129356 | 2/2001 |
| JP | 2001128990 A | 5/2001 |
| JP | 2001-190564 A | 7/2001 |
| JP | 2001-3400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |

(56) References Cited

FOREIGN PATENT DOCUMENTS

| WO | 0115614 A1 | 3/2001 |
|---|---|---|
| WO | 0154604 A1 | 8/2001 |
| WO | 2005110264 A3 | 4/2006 |

OTHER PUBLICATIONS

U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis pf Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/ Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 050206663 dated Feb. 27, 2006.
Int'l Search Report EP 05021197.8 dated Feb. 20, 2006.
Int'l Search Report EP 050217793 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 060067162 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated Jun. 30, 2011.
Int'l Search Report EP 11 161117.4 dated Jun. 30, 2011.
Int'l Search Report EP 11 161118.2 dated Oct. 12, 2011.

(56) References Cited

OTHER PUBLICATIONS

Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 11, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 15, 2004.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 2000, Thomas P. Ryan.
U.S. Appl. No. 12/336,970, filed Dec. 17, 2008, Paul R. Sremcich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chemov.
U.S. Appl. No. 13/108,129, filed May 16, 2011, Boris Chemov.
U.S. Appl. No. 13/108,152, filed May 16, 2011, Boris Chemov.
U.S. Appl. No. 13/108,177, filed May 16, 2011, Boris Chemov.
U.S. Appl. No. 13/108,196, filed May 16, 2011, Boris Chemov.
U.S. Appl. No. 13/108,441, filed May 16, 2011, Boris Chemov.
U.S. Appl. No. 13/108,468, filed May 16, 2011, Boris Chemov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chemov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.

* cited by examiner

OPEN VESSEL SEALING INSTRUMENT AND METHOD OF MANUFACTURING THE SAME

CROSS REFERENCE TO RELATED APPLICATIONS

This application is a continuation of U.S. patent application Ser. No. 13/306,553, filed Nov. 29, 2011, now U.S. Pat. No. 9,265,565, the entire content of which is incorporated by reference herein.

TECHNICAL FIELD

The present disclosure relates to an open vessel sealing instrument and method of manufacturing the same. More particularly, the present disclosure relates to plastic open vessel sealing instruments manufactured via a molding process to provide a simple, easy to use and low cost open vessel sealing instrument.

BACKGROUND

An electrosurgical forceps is a plier-like instrument which relies on mechanical action between its jaws to grasp, clamp and constrict vessels or tissue; so-called "open forceps" are commonly used in open surgical procedures. Open forceps utilize both mechanical clamping action and electrical energy to effect hemostasis by heating tissue and blood vessels to coagulate and/or cauterize tissue. Forceps of this type, e.g., open forceps, typically, include a pair of shafts that are pivotally coupled to one another. In a bipolar configuration, each shaft includes a respective jaw member at a distal end thereof having a respective seal plate of opposing electrical potential and configured to electrosurgically treat tissue. In a monopolar configuration, the seal plates (or one seal plate) are energized to a first potential and a return pad is energized to a different potential to complete the circuit allowing the forceps to operate in a monopolar fashion.

As is common with conventional forceps of this type, one or more non-conductive stop members are typically disposed on seal surfaces of the respective seal plates of the jaw members. In addition, a cutter or knife blade assembly is typically operably coupled to the forceps and utilized to sever or cut tissue subsequent to tissue being electrosurgically treated.

Manufacture of the above type of forceps is, typically, expensive. That is, stamping the material, e.g., surgical steel, that makes up the shaft is a relatively expensive process. Moreover, positioning the non-conductive stop member(s) on the seal surfaces of the respective seal plates is a complex process that usually requires, first, manufacturing the non-conductive stop members and, subsequently, gluing the non-conductive stop members into an aperture that was previously formed on the seal plates; other techniques include plasma vapor deposition. Further, operably coupling the cutter or knife blade assembly to one or both of the shafts of the forceps, typically, is a lengthy process that increases manufacturing costs.

In addition to the foregoing, because the electrosurgical forceps utilize electrical components, the forceps are not configured for multiple uses. That is, use and subsequent sterilization of the forceps is not part of the operative life cycle of the forceps. In other words, the forceps is, typically, disposed after a single use.

SUMMARY

An aspect of the present disclosure provides an open electrosurgical forceps for treating tissue. The forceps includes a pair of first and second shaft members each having a jaw member at a distal end thereof. The jaw members are movable from a first position in spaced relation relative to one another to at least one subsequent position wherein the jaw members cooperate to grasp tissue therebetween. Each of the jaw members includes an electrically conductive sealing plate for communicating electrosurgical energy through tissue held therebetween. One or both of the jaw members include(s) a respective knife channel defined along a length thereof. A cutting mechanism is adapted to selectively and removably couple to one of the first and second shaft members. The cutting mechanism includes a cutting trigger that is configured for selectively advancing a knife blade extending therefrom through the knife channels defined along the at least one jaw member. The knife blade is advanceable from a first position wherein the knife blade is disposed proximal to tissue held between the jaw members to at least one subsequent position wherein the knife blade is disposed distal to tissue held between the jaw members.

According to an aspect of the present disclosure, one of the first and second shaft members includes an elongated slot defined therein and aligned with the knife channel defined along the at least one jaw member. In this instance, the elongated slot is configured to facilitate coupling the cutting mechanism to the respective shaft member. The cutting trigger may extend perpendicular to the knife blade.

In certain instances, the open electrosurgical forceps may include an activation mechanism that is configured to selectively and removably couple to one of the first and second shaft members and is adapted to selectively couple to a source of electrosurgical energy via a cable.

The seal plates may be secured to the jaw members via one of a press-fit and friction-fit such that the seal plates are selectively and releasably coupleable to the respective jaw members.

An opening is disposed adjacent a proximal end of the respective jaw member of the selectively and removably shaft member that couples to the cutting mechanism. The opening is configured to receive the other jaw member.

The shaft member coupled to the cutting mechanism may include one or more stop features defined thereon and adjacent the respective jaw member to control the gap distance between the jaw members. Moreover, the other shaft member may include one or more corresponding stop members defined thereon and adjacent the respective jaw member. The corresponding stop member is configured to selectively engage the stop feature to limit rotation of the first and second shaft members with respect to one another. In certain instances, the stop feature may be a generally arcuate indent and the stop member is a generally cylindrical detent.

Each of the first and second shaft members may be made from plastic and formed via an injection molding process.

An aspect of the present disclosure provides an open electrosurgical forceps for treating tissue. The forceps includes a pair of first and second shaft members each having a jaw member at a distal end thereof. The jaw members are movable from a first position in spaced relation relative to one another to at least one subsequent position wherein the jaw members cooperate to grasp tissue therebetween. Each of the jaw members includes an electrically conductive sealing plate for communicating electrosurgical energy through tissue held therebetween. One of the jaw members includes a stop feature formed thereon and the other one of the jaw members includes a corresponding stop member formed thereon. The stop feature and stop member are configured to selectively engage one another to limit the amount of rotation of the first and second shaft members with respect to one another and defines a gap distance between the jaw members when moved to the subsequent position to grasp tissue.

According to another aspect of the present disclosure, the stop feature is a generally arcuate indent extending radially inward into a sidewall of the first shaft member adjacent the respective jaw member. The stop member may be a generally cylindrical detent extending radially outward from a sidewall of the opposite jaw member.

The open electrosurgical forceps may include a cutting mechanism that is adapted to selectively and removably couple to one of the first and second shaft members. The cutting mechanism includes a cutting trigger. The cutting trigger is configured to selectively advance a knife blade extending therefrom through respective knife channels defined along the jaw members from a first position wherein the knife blade is disposed proximal to tissue held between the jaw members to at least one subsequent position wherein the knife blade is disposed distal to tissue held between the jaw members. In certain instances, the cutting trigger may extend perpendicular to the knife blade.

An activation mechanism may be configured to selectively and removably couple to at least one of the first and second shaft members and adapted to selectively couple to a source of electrosurgical energy via a cable.

The seal plates may be secured to the jaw members via one of a press-fit and friction-fit such that the seal plates are selectively and releasably coupleable to the respective jaw members.

An opening is disposed adjacent a proximal end of the respective jaw member of the shaft member coupled to the cutting mechanism. The opening configured to receive the other jaw member.

Each of the first and second shaft members may be made from plastic and formed via an injection molding process.

Another aspect of the he present disclosure provides a method of manufacturing an open electrosurgical forceps. The method includes forming a pair of first and second shaft members each having a jaw member at a distal end thereof. Each jaw member is formed with a transverse aperture extending therethrough. The first shaft member includes a stop feature formed thereon and the second shaft includes a corresponding stop member formed thereon. The stop feature and stop member are configured to selectively engage one another to limit rotation of the first and second shaft members with respect to one another and define a gap distance between the jaw members when moved to the subsequent position to grasp tissue. Subsequently, the first and second shaft members are positioned in juxtaposed relation to each other. Thereafter, a pivot pin is pressed through each of the first and second shaft members to pivotably couple the first and second shafts to one another. Then, a cutting mechanism is coupled to at least one of the first and second shaft members. And, an activation mechanism is coupled to at least one the first and second shaft members.

BRIEF DESCRIPTION OF THE DRAWINGS

Various embodiments of the present disclosure are described hereinbelow with reference to the drawings, wherein.

DETAILED DESCRIPTION

Figure 1:
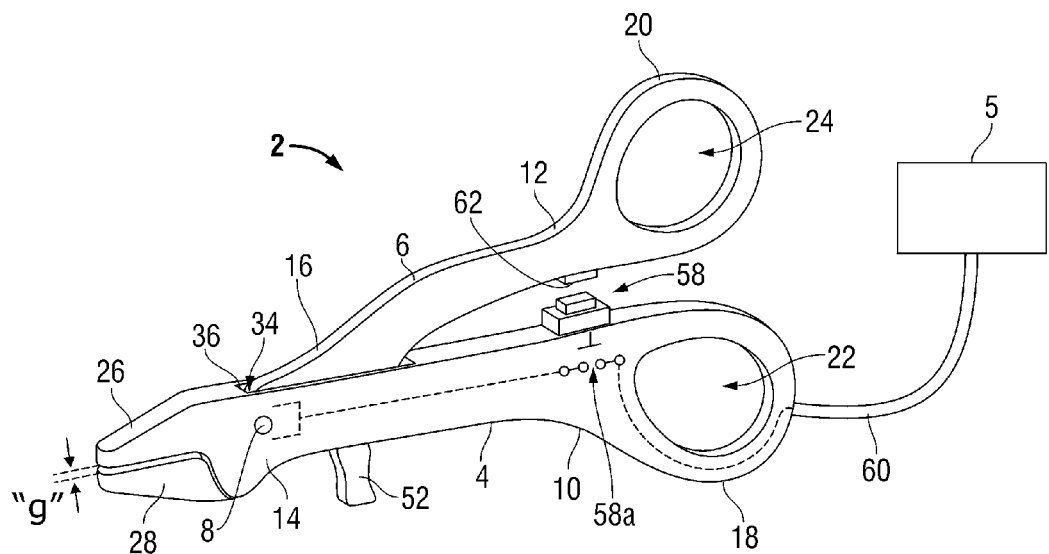
FIG. 1 is a side, perspective view of an open electrosurgical forceps according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Referring now to FIGS. 1-5, a forceps 2 for use with open surgical procedures is illustrated. Forceps 2 includes elongated shaft members 4 and 6 that are individually formed via an injection molding process and, subsequently, coupled to one another via a pivot pin 8; a manufacturing method of the forceps 2 is described in greater detail below.

Continuing with reference to FIGS. 1-4, shaft members 4 and 6 include respective proximal ends 10 and 12 and distal ends 14 and 16. In the drawings and in the descriptions which follow, the term "proximal", as is traditional, will refer to the end of the forceps 2 which is closer to the user, while the term "distal" will refer to the end which is further from the user.

Respective handles 18 and 20 are disposed at the proximal ends 10 and 12 and define finger holes 22 and 24 therethrough for receiving a finger of the user. As can be appreciated, finger holes 22 and 24 facilitate movement of the shafts 4 and 6 relative to one another, which, in turn, pivots a pair of opposing jaw members 26 and 28 from an open position wherein the jaw members 26 and 28 are disposed in spaced relation relative to one another (as best seen in FIG. 3) to a clamping or closed position wherein the jaw members 26 and 28 cooperate to grasp tissue therebetween (as best seen in FIG. 1).

Figure 3:
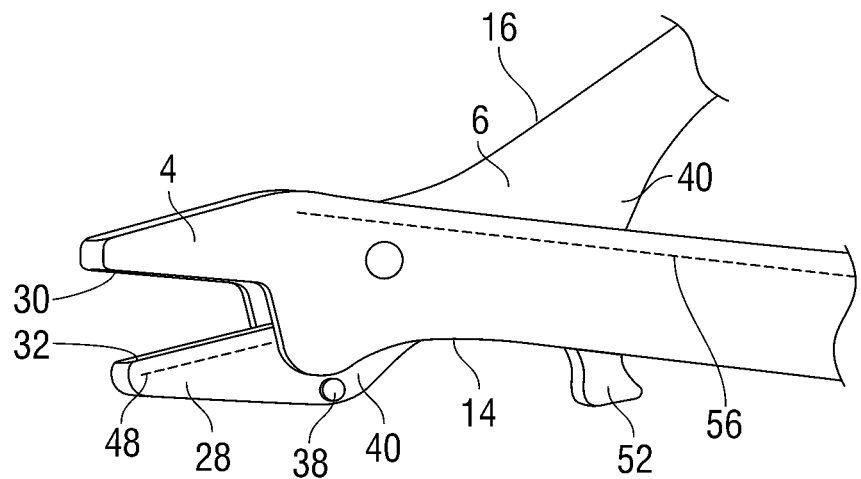
FIG. 3 is a partial, perspective view illustrating jaw members of the forceps depicted in FIG. 1 in an open configuration.

Jaw members 26 and 28 are disposed at respective distal ends 14 and 16 (FIGS. 1 and 3). Jaw members 26 and 28 are configured to grasp and, subsequently, electrosurgically treat tissue grasped therebetween. In the illustrated embodiment, forceps 2 includes a bipolar jaw configuration (e.g., the jaw members 26 and 28 are energized to opposite electrical potentials and operable to conduct electrosurgical energy through tissue held between the jaw members 26 and 28). A monopolar jaw configuration may also be utilized, e.g., one of the jaw members is energized to a first electrical potential and a remote return pad is energized to a different potential and positioned on a patient's skin.

Jaw members 26 and 28 include respective electrically conductive sealing plates 30 and 32 (FIGS. 2-4) for communicating electrosurgical energy through tissue held therebetween. Seal plates 30 and 32 are secured to the respective jaw members 26 and 28 via one or more suitable securement methods. In the illustrated embodiment, seal plates 30 and 32 are secured to respective jaw members 26 and 28 in either a press or friction fit manner. Having seal plates 30 and 32 that are selectively and releasably coupleable to the respective jaw members 26 and 28 may facilitate sterilization of a reusable forceps 2. For example, and in accordance with the instant disclosure, the seal plates 30 and 32 may be utilized with the forceps 2 and, subsequently, uncoupled therefrom for sterilization and future use with either the forceps 2 or another forceps. Accordingly, the seal plates 30 and 32 may be disposable, re-usable, and/or reposable.

Figure 2:
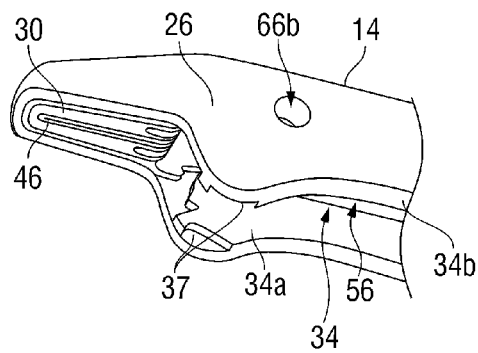
FIG. 2 is a partial, perspective view of a distal end of a first shaft member of the forceps depicted in FIG. 1.

A slot or opening 34 (FIGS. 1-2) of suitable configuration is defined adjacent a proximal end 36 of the jaw member 26. In one embodiment, opening 34 includes a generally elongated configuration and is defined by a pair of sidewalls 34a and 34b positioned at the proximal end 36 of the jaw member 26, as best seen in FIG. 2. The opening 34 is configured to receive jaw member 28 of the shaft member 6 during the manufacture and assembly of the forceps 2.

One or more stop features (FIG. 2) are defined on an interior of the sidewalls 34a and 34b and are disposed on the shaft member 4 adjacent jaw member 26. In one embodiment, the stop feature(s) is/are in the form of a pair of generally arcuate indents 37 that extend radially inward on each of the sidewalls 34a and 34b (see FIG. 2). Indents 37 are formed on the sidewalls 34a and 34b during the molding process of the shaft member 4. Alternatively, the indents 37 may be cut or notched out subsequent to forming the shaft member 4. The indents 37 are configured to selectively engage a pair of corresponding stop members 38 disposed on the shaft member 6 (See FIG. 3).

In one embodiment, stop members 38 are in the form of a pair detents 38 that extend radially outward from left and right sidewalls 40 (right sidewall not explicitly shown) of the shaft member 6 (see FIG. 1 in combination with FIG. 3). Detents 38 may have any suitable configuration, e.g., square, cylindrical, rectangular, etc. In the illustrated embodiment, detents include a generally cylindrical configuration. Detents 38 are formed on left sidewall and the right sidewalls 40 during the molding process of the shaft member 6. Alternatively, the detents 38 may be secured to left and right sidewalls 40 subsequent the formation of the shaft member 6.

The indents 37 and detents 38 are configured to selectively engage one another to limit the rotation of the shaft members 4 and 6 with respect to one another. Moreover, indents 37 and detents 38 are configured to facilitate gripping and manipulation of tissue and to define a gap distance "g" between opposing jaw members 26 and 28 during sealing of tissue, see FIG. 1 for example. In one embodiment, the separation distance during sealing or the gap distance "g" is within the range of about 0.001 inches to about 0.006 inches.

Figure 4:
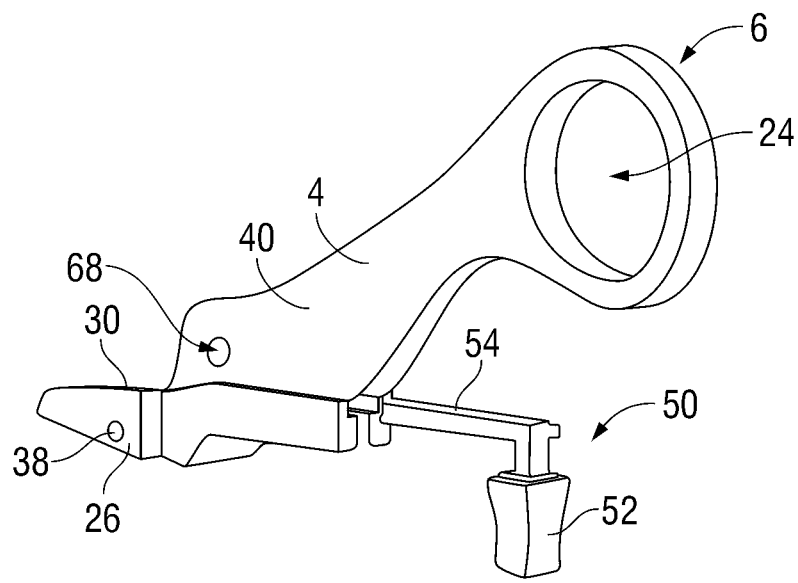
FIG. 4 is a rear, perspective view illustrating a back end of the first shaft member.

Each jaw member 26 and 28 includes a respective knife channel 46 (FIG. 2) and 48 (in FIG. 3 knife channel 48 is shown in phantom) defined along a length thereof. In particular, jaw members 26 and 28 include respective knife channels 46 and 48 that are configured to allow reciprocation of a cutting mechanism 50 (or component thereof) therewithin (FIG. 4). In certain embodiments, the knife channels 46 and 48 may be tapered or some other configuration that facilitates or enhances cutting of the tissue during reciprocation of the cutting mechanism 50 in the distal direction. Moreover, the knife channels 46 and 48 may be formed with one or more safety features (not shown) that prevent the cutting mechanism 50 from advancing through the tissue until the jaw members 26 and 28 are closed about the tissue.

Cutting mechanism 50 is adapted to selectively and removably couple to either shaft member 4 or 6. In the illustrated embodiment, the cutting mechanism 50 is shown coupled to the shaft 4. Cutting mechanism 50 includes a cutting trigger 52 that is configured to selectively advance a knife blade 54 extending therefrom through the knife channels 46 and 48. In particular, knife blade 54 is advanceable from a first position, wherein the knife blade 54 is disposed proximal to tissue held between the jaw members 26 and 28, to one or more subsequent positions, wherein the knife blade 54 is disposed distal to tissue held between the jaw members 26 and 28. For ease of operation, the cutting trigger 52 is shown oriented perpendicular with respect to the knife blade 54.

In some embodiments, an elongated slot 56 (FIGS. 2-3) is defined along one or both shaft members 4 and 6. For illustrative purposes, the elongated slot 56 is shown on shaft 4. Elongated slot 56 is aligned with the knife channels 46 and 48 defined within jaw members 26 and 28. The elongated slot 56 is configured to facilitate coupling the cutting mechanism 50 to the shaft member 4 and reciprocating the knife blade 54 through the knife channels 46 and 48 defined along the jaw members 26 and 28. That is, the elongated slot 56 helps maintain the knife blade 54 in substantial alignment with the knife channels 46 and 48.

In accordance with the instant disclosure, the cutting mechanism 50 may be utilized with the forceps 2 and, subsequently, uncoupled therefrom for sterilization and future use with either the forceps 2 or another forceps. Accordingly, the cutting mechanism 50 may be disposable, re-usable, and/or reposable.

With reference again to FIG. 1, an activation mechanism 58 is configured to selectively and removably couple to either shaft members 4 or 6. For illustrative purposes, the activation mechanism 58 is shown selectively and removably coupled to shaft 4 via a snap, press or friction fit manner. Activation mechanism 58, e.g., a push-button switch, relay or the like, is configured to provide electrosurgical energy to the seal plates 30 and 32. In particular, the activation mechanism 58 is configured such that when the jaw members 26 and 28 are moved to the clamping position, the shaft member 6 contacts or "presses" the activation mechanism 58, which, in turn, closes a circuit 58a of the forceps 2 (FIG. 1). In one particular embodiment, an optional extension pin 62 is operably disposed on shaft 6 and is configured to contact the activation mechanism 58. The extension pin 62 may be configured such that the activation mechanism 58 does not close the circuit 58a until a predetermined gap distance "g" has been achieved between the jaw members 26 and 28.

Activation mechanism 58 is configured to electrically communicate with a cable assembly 60 that couples the circuit 58a to an electrosurgical energy source, e.g., a generator 5. The activation mechanism 58 may be coupled to shaft 4. The cable assembly 60 is configured to provide electrosurgical energy to each of the seal plates 30 and 32 when the activation mechanism 58 is pressed and the forceps 2 is coupled to generator 5. The cable assembly 60 is adapted to selectively couple to the generator 5 via a cable 64 (FIG. 1). Cable 64 may be configured to releasably couple to the forceps 2.

Alternately, the forceps 2 may be battery-powered. In this instance, activation mechanism 58 may be configured to electrically communicate with a battery (not explicitly shown) that is configured to provide electrosurgical energy to the seal plates 32, 34.

In accordance with the instant disclosure, the activation mechanism 58 and/or cable assembly 60 may be utilized with the forceps 2 and, subsequently, uncoupled therefrom for sterilization and future use with either the forceps 2 or another forceps. Accordingly, the activation mechanism 58 and/or cable assembly 60 may be disposable, re-usable, and/or reposable.

In one particular embodiment, to facilitate coupling and uncoupling the activation mechanism 58 and the cable assembly 60 to and from the forceps 2, the activation mechanism 58 and cable assembly 60 may be configured as a unitary component.

Operation of the forceps 2 is similar to conventional open forceps. In particular, tissue is positioned between the jaw members 26 and 28. Thereafter, shaft members 4 and 6 are moved toward one another until detent 38 contacts indent 36, which corresponds to jaw members 26 and 28 being in a clamped configuration separated by a gap distance "g". When tissue is quite thick, however, the detent 38 and indent 36 may not contact one another. In this instance, for example, the detent 38 and indent 36 may contact one another only after tissue has been "cooked." In one embodiment, this gap distance "g" allows the extension 62 to contact the activation mechanism 58, which, in turn, allows electrosurgical energy to flow to the seal plates 30 and 32. Unlike conventional forceps, however, that utilize stop members on the seal plates of the jaw members, the unique configuration of the indents 37 and corresponding detents 38 provide a simple and cost effective method of maintaining a specific gap distance "g" between the jaw members 26 and 28. And, the likelihood of the stop members, e.g., detents 38, becoming dislodged is diminished, if not eliminated.

Figure 5:
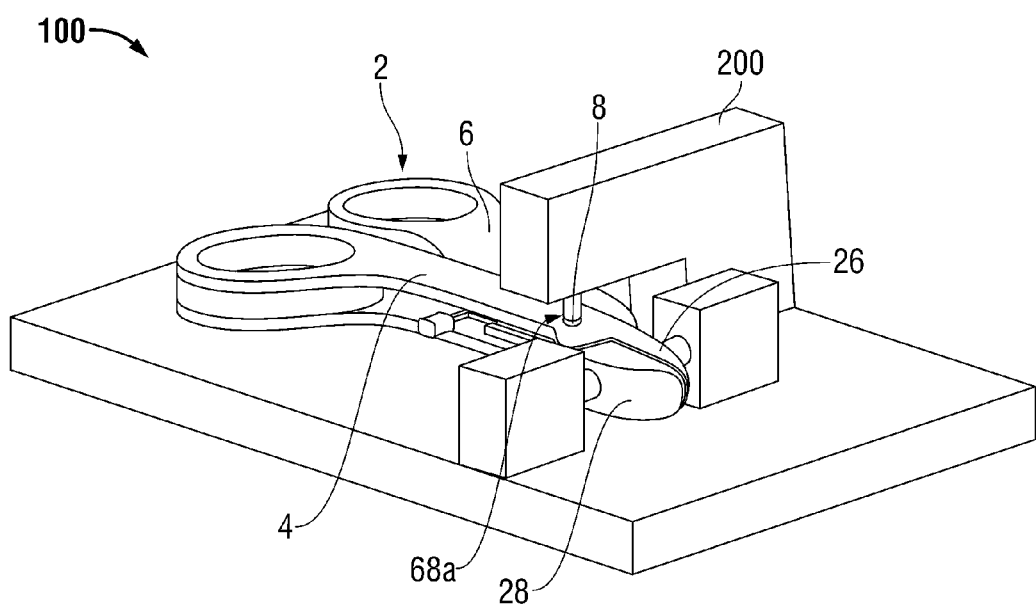
FIG. 5 is perspective view illustrating a step of a manufacturing process of the forceps depicted FIG. 1.

With reference now to FIG. 5, a method 100 of manufacturing the forceps 2 is illustrated. Forceps 2 is formed by an injection molding process that produces a forceps 2 that is disposable, re-usable or reposable. Briefly, an injection molding process, typically, includes one or more suitable materials, e.g., thermoplastic, thermosetting plastic material, etc., that is fed into one or more suitable holding vessels, e.g., a heated barrel, and, subsequently, mixed, and, thereafter, forced into a pair of mold cavities where the plastic is allowed to cool and harden to the configuration of the mold cavities. The mold cavities are configured to provide a pair of shaft members 4 and 6. As noted above, shaft member 4 may be formed with indents 37 formed thereon and the shaft member 6 is formed with detents 38 formed thereon such that the indents 37 and detents 38 may function in a manner as described above.

Shaft member 4 is formed with opening 34 therethrough to receive jaw member 28 of the shaft member 6 therethrough during the manufacture and assembly of forceps 2. In the illustrated embodiment, the opening 36 extends perpendicularly to apertures 66a (in FIG. 5 aperture 66a is shown engaged with pivot pin 8 and, as such, is not visible), 66b (FIG. 2) and 68 formed on respective shaft members 4 and 6 (FIG. 4).

In one embodiment, shaft 4 is formed with respective apertures 66a and 66b of suitable configuration through sidewalls 34a and 34b (FIG. 2). Likewise, shaft 6 is formed with an aperture 68 of suitable configuration through left and right sidewalls 40. Unlike shaft 6 that includes aperture 68 being formed through left and right sidewalls 40 during the aforementioned molding process, aperture 66b is formed through the sidewall 34b during the aforementioned molding process, as best seen in FIG. 2, and aperture 66a is formed through the sidewall 34a subsequent to the molding process; this facilitates coupling the shafts 4 and 6 to one another during the manufacturing process of the forceps 2.

In one embodiment, to assemble the forceps 2, shafts 4 and 6 are positioned in juxtaposed relation to each other, see FIG. 5. Thereafter, pivot pin 8 is pressed through each of the apertures 66b and 68, via one or more suitable pressing device(s) 200, to pivotably couple the shafts members 4 and 6 to one another. In accordance with the present disclosure, this pressing sequence provides the final aperture 66a through the sidewall 34a. This allows for subsequent removal of the pivot pin 8. Thus, the forceps 2 may be utilized as described above, thereafter the pivot pin 8 may be removed and the forceps 2 may be sterilized for future use.

From the foregoing and with reference to the various figure drawings, those skilled in the art will appreciate that certain modifications can also be made to the present disclosure without departing from the scope of the same. For example, it may prove advantageous to manufacture and, subsequently, ship the forceps 2 in a "ready-to-use" configuration, e.g., the forceps 2 is shipped pre-assembled. Alternatively, the forceps 2 may be manufactured and shipped in an "un-assembled" configuration. In this instance, one or more of the operative components of the forceps 2 may be shipped uncoupled thereto. For example, the cutting mechanism 50 may be shipped as a separate component and coupled to the forceps 2 in the surgical environment. Or, each component of the forceps 2 may be shipped together and, subsequently, coupled to one another in the surgical environment, e.g., the forceps 2 may be manufactured and sold as a kit.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A forceps, comprising:
   first and second shaft members, each of the first and second shaft members having a handle at a proximal end thereof and a jaw member at a distal end thereof, the handles of the first and second shaft members movable relative to one another to pivot the first and second shaft members in relation to one another so that the jaw members cooperate to grasp tissue therebetween, each of the jaw members including an electrically conductive sealing plate configured to communicate electrosurgical energy through tissue held therebetween; and
   a cutting mechanism received within an elongated slot defined by at least one of the first and second shaft members, the cutting mechanism slidably removable in a longitudinal direction from the elongated slot to separate the cutting mechanism from the forceps.

2. The forceps of claim 1, further comprising an activation mechanism coupled to the first shaft member and adapted to connect to a source of electrosurgical energy, the activation mechanism configured to communicate electrosurgical energy to at least one of the sealing plates in response to contact with the second shaft member.

3. The forceps of claim 1, wherein the sealing plates are removably coupled to the jaw members by press-fit, friction-fit, or combinations thereof.

4. The forceps of claim 1, wherein at least one first and second shaft members is formed via injection molding.

5. The forceps of claim 1, wherein the first shaft member includes at least one stop feature configured to control the gap distance between the jaw members.

6. The forceps of claim 5, wherein the second shaft member includes at least one stop member configured to selectively engage the at least one stop feature, wherein the at least one stop feature and the at least one stop member are configured to engage one another to limit pivoting of the first and second shaft members.

7. The forceps of claim 1, wherein each of the first and second shaft members is made from plastic.

8. The forceps of claim 1, wherein the cutting mechanism includes a cutting trigger configured to selectively advance a knife blade extending therefrom through at least one knife channel defined between the jaw members.

9. The forceps according to claim 8, wherein the cutting trigger extends transverse to the knife blade.

10. The forceps according to claim 1, wherein the elongated slot is aligned with at least one knife channel defined in at least one of the jaw members facilitating advancement of a knife blade of the cutting mechanism through the at least one knife channel.

11. The forceps according to claim 1, wherein the elongated slot is disposed proximal to the jaw members such that the cutting mechanism extends through the elongated slot into the at least one knife channel.

12. The forceps according to claim 1, wherein the cutting mechanism is made from sterilizable materials and is reusable.

* * * * *